(12) United States Patent
Arnold et al.

(10) Patent No.: US 6,413,971 B1
(45) Date of Patent: *Jul. 2, 2002

(54) FUSED BICYCLIC PYRIMIDINE DERIVATIVES

(75) Inventors: Lee Daniel Arnold, Westborough, MA (US); Mikel Paul Moyer, Old Lyme; Susan Beth Sobolov-Jaynes, Ivoryton, both of CT (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,602

(22) PCT Filed: Nov. 5, 1997

(86) PCT No.: PCT/IB97/01393

§ 371 (c)(1),
(2), (4) Date: May 19, 1999

(87) PCT Pub. No.: WO98/23613

PCT Pub. Date: Jun. 4, 1998

Related U.S. Application Data

(60) Provisional application No. 60/031,862, filed on Nov. 27, 1996, and provisional application No. 60/041,846, filed on Apr. 9, 1997.

(51) Int. Cl.[7] .......................... A61K 31/519; A61P 3/10; C07D 487/04
(52) U.S. Cl. ...................... 514/258; 544/117; 544/279; 544/280
(58) Field of Search ................................ 544/279, 280; 514/258

(56) References Cited

U.S. PATENT DOCUMENTS

| 5,804,685 A | * | 9/1998 | Yuan et al. .................. 544/280 |
| 5,847,136 A | * | 12/1998 | Yuan et al. .................. 544/280 |
| 6,096,749 A | * | 8/2000 | Traxler et al. .............. 544/280 |

FOREIGN PATENT DOCUMENTS

| WO | 94/13676 | 6/1994 |
| WO | 95/15758 | 6/1995 |
| WO | 95/19774 | 7/1995 |
| WO | 95/23141 | 8/1995 |
| WO | 96/31510 | 10/1996 |
| WO | 96/40142 | 12/1996 |
| WO | 97/02266 | 1/1997 |

* cited by examiner

*Primary Examiner*—Robert W. Ramsuer
(74) *Attorney, Agent, or Firm*—Peter C. Richardson; Paul H. Ginsburg; Jeffrey N. Myers

(57) ABSTRACT

The invention relates to compounds of the formula

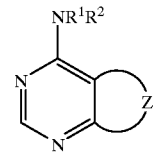

I and to pharmaceutically acceptable salts thereof, wherein $R^1$, $R^2$ and Z are as defined herein. The invention also relates to pharmaceutical compositions containing the compounds of formula I and to methods of using said compounds in the treatment of hyperproliferative diseases such as cancer.

22 Claims, No Drawings

FUSED BICYCLIC PYRIMIDINE DERIVATIVES

This is a national stage filing under 35 USC Section 371 of PCT/IB97/01393, filed Nov. 5, 1997, which claimed priority of U.S. Provisional Application Nos. 60/031,862 and 60/041,846 filed Nov. 27, 1996 and Apr. 9, 1997, respectively.

BACKGROUND OF THE INVENTION

This invention relates to novel bicyclic pyrimidine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Compounds that are useful in the treatment of hyperproliferative diseases are also disclosed in the following co-pending patent applications: PCT international patent application number PCT/IB97/100675 (filed Jun. 11, 1997), United States provisional patent application No. 60/028881 (filed Oct. 17, 1996), PCT international patent application number PCT/IB97/00584 (filed May 22, 1997), U.S. patent application Ser. No. 08/653,786 (filed May 28, 1996), PCT international patent application publication number WO 96/40142 (published Dec. 19, 1996), and PCT international patent application publication number WO 95/23141 (published Aug. 31, 1995). Each of the foregoing United States and PCT international patent applications is incorporated herein by reference in its entirety.

It is known that a cell may become cancerous by virtue of the transformation of a portion of its DNA into an oncogene (i.e., a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. It is known that such kinases are often aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995).

It is known that polypeptide growth factors such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995). Agents, such as the compounds of the present invention, that are capable of binding to or modulating the KDR/FLK-1 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

SUMMARY OF THE INVENTION

The present invention relates to compounds of the formula

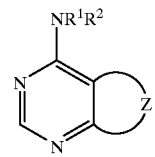

I and to pharmaceutically acceptable salts thereof, wherein;

Z is a group of the formula

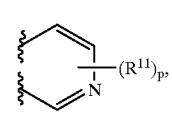

(Ia)

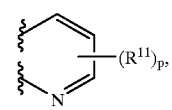

(Ib)

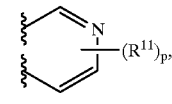

(Ic)

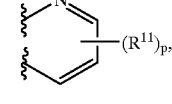

(Id)

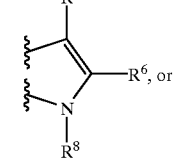

(Ie)

-continued (If)

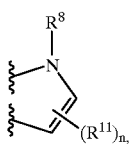

wherein n is an integer from 0 to 2 and p is an integer from 0 to 3;

$R^1$ is H, $C_1$–$C_6$ alkyl or —C(O)($C_1$–$C_6$ alkyl);

$R^2$ is phenyl or 1H-indazol-5-yl, wherein said groups are optionally substituted by 1 to 3 $R^5$ substituents, or $R^2$ is a group of the formula (Ii) or (Ij)

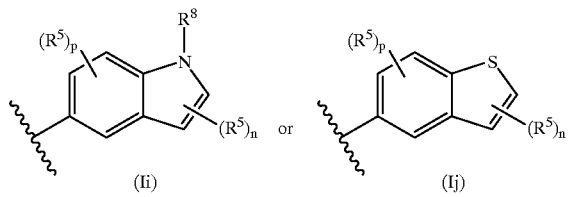

(Ii)

(Ij)

wherein p is an integer from 0 to 3 and n is an integer from 0 to 2;

or $R^1$ and $R^2$ are taken together to form a group of the formula (Ik)

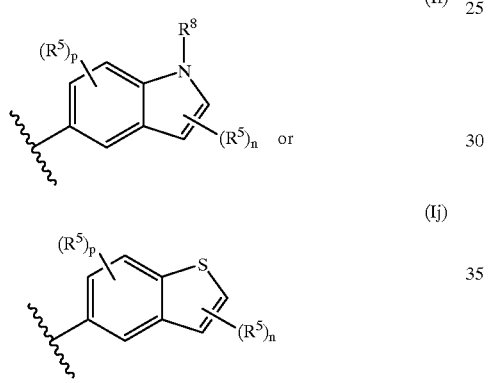

(Ik)

wherein the dashed line indicates a single or double bond and m is an integer from 0 to 4;

each $R^3$ is independently H, —C(O)$OR^9$, or $C_1$–$C_6$ alkyl wherein said alkyl is optionally substituted by halo, —$OR^9$, —$NR^9R^{10}$ or —C(O)$OR^9$;

$R^4$ is $R^3$ —$OR^9$, or —$NR^9R^{10}$;

each $R^5$ is independently halo, cyano, $C_1$–$C_6$ alkyl, $C_2$–$C_6$ alkenyl, $C_2$–$C_6$, alkynyl, —$OR^9$, —$NR^9R^{10}$, nitro, or $C_6$–$C_{10}$ aryl wherein said alkyl, alkenyl, alkynyl and aryl $R^5$ groups are optionally substituted by 1 to 3 substituents independently selected from halo, nitro, $C_1$–$C_4$ alkyl and —$OR^9$;

$R^6$ and $R^7$ are independently H or $R^5$;

$R^8$ is H, —$SO_2$($C_6$–$C_{10}$ aryl), —$(CH_2)_q$(5–10 membered heterocyclyl), $C_2$–$C_6$ alkenyl, $C_1$–$C_6$ alkyl, —$(CH_2)_q$ $(CH_2)_q(C_1$–$C_6$ alkoxy), —$(CH_2)_q(C_1$–$C_6$ alkoxy), —C(O)($C_1$–$C_6$ alkoxy), or —$SO_2$($C_1$–$C_4$ alkyl) wherein each q is independently an integer from 2 to 4;

each $R^9$ and $R^{10}$ is independently H or $C_1$–$C_6$ alkyl; and, $R^{11}$ is trifluoromethyl, halo, nitro, —$OR^9$, —$NR^9R^{10}$, cyano, $C_1$–$C_4$ alkyl, —S(O)$_xR^9$ wherein x is an integer from 0 to 2, —C(O)$OR^9$, —OC(O)($C_1$–$C_4$ alkyl), —C(O)$NR^9R^{10}$), —$NR^9$C(O)($C_1$–$C_4$ alkyl), —C(O) $NHSO_2$($C_1$–$C_4$ alkyl), —$NHCH_2$C(O)$NR^9R^{10}$, —NHC(O)($C_1$–$C_4$ alkoxy), —NHOC(O)($C_1$–$C_4$ alkyl), —$NR^9OR^{10}$, anilino, pyrrolidinyl, piperidinyl, azido, guanidino, morpholino, phenyl, —C(O)($C_1$–$C_6$ alkyl), benzenesulfonyl, allyl, thiophenyl, piperazinyl, 4-($C_1$–$C_4$ alkyl)-piperazinyl, phenyftnio, benzenesulphonamido, 2-oxopyrrolidin-1-yl, 2,5dioxopyrrolidin-1-yl, phenoxy, benzoyloxy, benzoylamino, —$(CH_2)_wO(CH_2)_vOR^9$, —O$(CH_2)_wO$ $(CH_2)_vOR^9$, —O$(CH_2)_wC(O)OR^9$, —O$(CH_2)_wC(O)$ $NR^9R^{10}$, —$(CH_2)_wS(CH_2)_vOR^9$—NH$(CH_2)_vO(C_1$–$C_4$ alkyl), —NH$(CH_2)_w(C_6$–$C_{10}$ aryl), —NHC(O)$(CH_2)_w$ ($C_1$–$C_4$ alkoxy), or —O$(CH_2)_w(C_6$–$C_{10}$ aryl), wherein w is an integer from 1 to 4 and v is an integer from 2 to 4, and wherein the alkyl, heterocyclic, and aryl moieties of the foregoing $R^{11}$ groups are optionally substituted by 1 or 2 substituents independently selected from the group consisting of halo, $C_1$–$C_4$ alkyl, —$OR^9$—$NR^9R^{10}$, —C(O)$OR^9$, —OC(O)($C_1$— $C_4$ alkyl), —C(O)$NR^9R^{10}$, —NHC(O)($C_1$–$C_4$ alkyl), nitro, imidazolyl, piperidino, morpholino, and piperazinyl;

with the proviso that where Z is a group of the formula (Ie), and $R^2$ is phenyl, then said phenyl is substituted by 1 to 3 substituents independently selected from $C_1$–$C_6$ alkyl, $C_2$–$C_6$ alkynyl and halo, and one of $R^4$ and $R^7$ is halo or H and the other is as defined above; and, with the further proviso that where Z is a group of the formula (Ia), (Ib), (Ic) or (Id), and $R^2$ is phenyl, then said phenyl is substituted by $C_2$–$C_6$ alkynyl.

Preferred compounds of formula I include those wherein $R^2$ is optionally substituted phenyl. More preferred are those compounds of formula I wherein $R^2$ is phenyl substituted by $C_2$–$C_6$ alkynyl, in particular ethynyl.

Other preferred compounds of formula I include those wherein Z is a pyrrolo moiety of formula (Ie) or (If).

Other preferred compounds of formula I include those wherein $R^1$ and $R^2$ are taken together to form an indole or indoline moiety of formula (1k), Specific preferred compounds of formula I include the following:

4-(6-Chloro-2,3dihydro-indol-1-yl)-7H-pyrrolo[2,3-d] pyrimidine;

4-(6-Methyl-2,3dihydro-indol-1-yl)-7H-pyrrolo[2,3-d] pyrimidine;

4 (6-Chloro-5-fluoro-2,3dihydryo-indol-1-yl)-7H-pyrrolo [2,3]pyrimidine:

1-(4-m-Tolylamino-pyrrolo[2,3-d]pyrimidin-7-yl)-ethanone;

4-(6Chloro-2,3-dihydro-indol-1-yl)-pyrido[3,4-d] pyrimidine;

4-(6-Bromo-5chloro-2,3-dihydro-indol-1-yl)-pyrido[3,4-d] pyrimidine;

4-(6-Fluoro5chloro-2,3-dihydro-indol-1-yl)-pyrido[3,4-d] pyrimidine;

4(6lodo-2,3-dihydro-indol-1-yl)-pyrido[3,4-d]pyrimidine;
(7-Benzenesulfonyl-7H-pyrrolo[2,3-d]pyrimidin-4-yl)-(3ethynyl-phenyl)-amine;
4-(6-Chloro-2,3-dihydro-indol-1-yl)-5H-pyrrolo[3,2-d]pyrimidin-6-ol;
(3-Ethynyl-phenyl)-[7(2morpholin-4-yl-ethyl)-7H-pyrrolo[2,3-d]pyrimidin-4-yl]-amine;
(3-Ethynyl-phenyl)-[7-(2-methoxy-ethyl)-7H-pyrrolo[2,3-d]pyrimidin-4-yl]-amine;
(3Ethynyl-phenyl)-{7[2-(2-methoxy-ethoxy)ethyl]-7H-pyrrolo[2,3-d]pyrmidin4-yl}amine;
(7-Allyl-pyrrolo[2,3-d]pyrimidin-4-yl)-(3ethynyl-phenyl)-amine;
N-(5lodo-7H-pyrrolo[2,3-d]pyrimidin-4-yl)-N-m-tolyl-acetamide;
4-(6-Chloro-2,3dihydro-indol-1-yl)6-methyl-pyrido[3,4-d]pyrimidine;
4-(6-Bromo-5-fluoro-2,3dihydro-indol-1-yl)6methyl-pyrido[3,4-d]pyrimidine;
4-(6-Chloro5-fluoro-2,3dihydro-indol-1-yl)-6-methyl-pyrido[3,4-d]pyrimidine;
4-(6-lodo-2,3dihydro-indol-1-yl)-6-methyl-pyrido[3,4]pyrimidine;
4-(4-Bromo-7-methyl-2,3-dihydro-indol-1-yl)6-methyl-pyrido[3,4-d]pyrimidine;
4-(6-Bromo-7-methyl-2,dihydro-indol-1-yl)-6-methyl-pyrido[3,4-d]pyrimidine;
4-(6,7-Dimethyl-2,3dihydro-indol-1-yl)pyrido[3,4-d]pyrimidine;
(3-Ethynyl-phenyl)pyrido[3,4-d]pyrimidin-4-yl-amine;
Benzo[b]thiophen-5yl-pyrido[3,4-d]pyrimidin4-yl-amine;
(3-Ethynyl-phenyl)-(5-tolyl-7H-pyrrolo[2,3-d]pyrimidin4-yl)-amine;
(3-Ethynyl-phenyl)-(5-thiophen-2-yl-7H-pyrrolo[2,3-d]pyrimidin-4-yl)-amine;
(3-Ethynyl-phenyl)-[5-(4-methoxy-phenyl)-7H-pyrrolo[2,3-d]pyrimidin-4-yl]-amine;
(3-Ethynyl-phenyl)-[5-(3nitro-phenyl)7H-pyrrolo[2,3-d]pyrimidin-4-yl]-amine;
[5-(4-chloro-phenyl)-7H-pyrrolo[2,3-d]pyrimidin-4-yl]-(3-ethynyl-phenyl)-amine;
(3-Bromo-phenyl)-(6-bromo-5-phenyl-7H-pyrrolo[2,3-d]pyrimidin-4-yl)-amine; and the pharmaceutically acceptable salts of the foregoing compounds.

The invention also relates to a pharmaceutical composition for the treatment of a hyperproliferative disorder in a mammal which comprises a therapeutically effective amount of a compound of formula I, or a pharmaceutically acceptable salt thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of a hyperproliferative disorder in a mammal which comprises a therapeutically effective amount of a compound of formula I or a pharmaceutically acceptable salt thereof, in combination with an anti-tumor agent selected from the group consisting of mitotic inhibitors, alkylating agents, anti-metabolites, intercalating antibiotics, enzymes, topoisomerase inhibitors, biological response modifiers, anti-hormones, and anti-androgens, and a pharmaceutically acceptable carrier.

The invention also relates to a pharmaceutical composition for the treatment of pancreatitis or kidney disease (including proliferative glomerulonephritis and diabetes-induced renal disease) in a mammal which comprises a therapeutically effective amount of a compound of formula I or a pharmaceutically acceptable salt thereof, and a pharmaceutically acceptable carrier.

The invention also relates to a pharmaceutical composition for the prevention of blastocyte implantation in a mammal which comprises a therapeutically effective amount of a compound of formula I or a pharmaceutically acceptable salt thereof, and a pharmaceutically acceptable carrier.

The invention also relates to a pharmaceutical composition for treating a disease related to vasculogenesis or angiogenesis in a mammal which comprises a therapeutically effective amount of a compound of formula I or a pharmaceutically acceptable salt thereof, and a pharmaceutically acceptable carrier. In one embodiment, said pharmaceutical composition is for treating a disease selected from the group consisting of diabetes, diabetic retinopathy, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula I or a pharmaceutically acceptable salt thereof. In one embodiment, said method relates to the treatment of cancer such as brain, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula I, or a pharmaceutically acceptable salt thereof, in combination with an anti-tumor agent selected from the group consisting of mitotic inhibitors, alkylating agents, anti-metabolites, intercalating antibiotics, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of the compound of formula I or a pharmaceutically acceptable salt thereof.

The invention also relates to a method of preventing blastocyte implantation in a mammal which comprises administering to said mammal a therapeutically effective amount of the compound of formula I or a pharmaceutically acceptable salt thereof.

The invention also relates to a method of treating diseases related to vasculogenesis or angiogenesis in a mammal which comprises administering to said mammal an effective amount of a compound of formula I, or a pharmaceutically acceptable salt thereof. In one embodiment, said method is for treating a disease selected from the group consisting of diabetes, diabetic retinopathy, hemangioma, glioma, melanoma, Kaposi's sarcoma and ovarian, breast, lung, pancreatic, prostate, colon and epidermoid cancer.

Patients that can be treated with compounds of the formula I, and the pharmaceutically acceptable salts of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for cyclic moieties at least three carbon atoms are required in said alkyl group.

The term "alkoxy", as used herein, unless otherwise indicated, includes O-alkyl groups wherein "alkyl", is as defined above.

The term "aryl", as used herein, unless otherwise indicated, includes an organic radical derived from an aromatic hydrocarbon by removal of one hydrogen, such as phenyl or naphthyl.

The term "5–10 membered heterocyclyl", as used herein, unless otherwise indicated, includes aromatic and non-aromatic heterocyclic groups containing one or more heteroatoms each selected from O, S and N, wherein each heterocyclic group has from 5–10 atoms in its ring system. The heterocyclic groups include benzo-fused ring systems and ring systems substituted with one or more oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula I that are acidic in nature, are capable of forming base salts with various pharmacologically acceptable cations. Examples of such salts include the alkali metal or alkaline earth metal salts and particularly, the sodium and potassium salts.

Certain compounds of formula I may have asymmetric centers and therefore exist in different enantiomeric forms. This invention relates to the use of all optical isomers and stereoisomers of the compounds of formula I and mixtures thereof. The compounds of formula I may also exist as tautomers. This invention relates to the use of all such tautomers and mixtures thereof.

DETAILED DESCRIPTION OF THE INVENTION

The preparation of the compounds of the present invention is illustrated in the following Schemes 1 and 2.

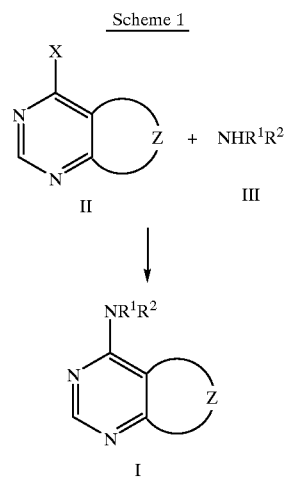

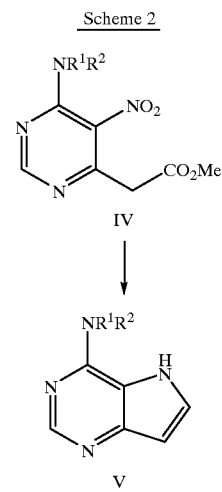

The compounds of the present invention are readily prepared according to synthetic methods familiar to those skilled in the art. Such methods are disclosed in PCT international patent application publication number WO 96/40142 (published Dec. 19, 1996), referred to above, and in PCT international application publication numbers WO 95/19774 (published Jul. 27, 1995) and WO 95/19970 (published Jul. 27, 1995), each of which is incorporated herein by reference.

Scheme 1 illustrates the coupling of the bicyclic compound of formula II with the amine of formula III to provide the compound of formula I. In the compounds of formulas II and III, X is hydroxy or chloro and Z. $R^1$ and $R^2$ are as defined above. In general, the compound of formula II is coupled with the amine of formula III in a solvent, such as a $C_1$–$C_6$ alcohol, dimethylformamide (DMF), N-methylpyrrolidin-2-one (NMP), chloroform, acetonitrile, tetrahydrofuran (THF), dimethylsulfoxide (DMSO), 1,4-dioxane or pyridine, optionally in the presence of a base, such as pyridine or triethylamine, and optionally in the presence of pyridine hydrochloride as a catalyst, under an inert atmosphere, such as dry nitrogen gas, at a temperature of from ambient to reflux temperature, preferably 80–125° C., for a period of about 2 hours to 72 hours.

The bicyclic compound of formula II is prepared according to synthetic methods known to those skilled in the art. Such methods are disclosed in WO 95/19774 and WO 95/19970, referred to above. Other methods of preparing the compounds of formula II are also disclosed in PCT international application publication number WO 92/12718 (published Aug. 6, 1992), A. Petric et al., Fur Chemie 114, 615–624 (1983) and Nucleic Acids Research, v. 12, no. 2 (1984). Where the compound of formula III is an optionally substituted indole or indoline moiety, such compounds can be prepared according to one or more methods known to those skilled in the art. Such methods are described in PCT international patent application publication number WO 95/23141, referred to above, and in W. C. Sumpter and F. M. Miller, "Heterocylic Compounds with Indole and Carbazole Systems," in volume 8 of "The Chemistry of Heterocyclic Compounds", Interscience Publishers Inc., New York (1954). Optional substituents can be included as appropriate before or after the coupling step illustrated in Scheme 1. Prior to the coupling step, primary and secondary amino moieties (other than the amine of formula III) are preferably protected using a nitrogen protecting group known to those skilled in the art. Such protecting groups and their use are described in T. W. Greene and P. G. M. Wuts, "Protective Groups in Organic Synthesis," Second Edition, John Wiley & Sons, New York, 1991.

Scheme 2 illustrates the cyclization of the compound of formula IV (wherein Me means methyl) to provide the compound of formula V. This illustrates the introduction of the Z moiety in the compound of formula I after the amino (—$NR^1R^2$) moiety has been coupled with the pyrimidine ring. .While Scheme 2 illustrates the formation of a pyrrolo [3,2-d]pyrimidine ring system, other ring systems can be made by one or more analogous methods disclosed in WO 90/19774, referred to above. In Scheme 2, the compound of formula IV, in an alcoholic solvent, such as ethanol, is catalytically hydrogenated using an appropriate catalyst, such as 10% palladium on carbon, under an $H_2$ atmosphere at ambient temperature for a period of about three hours to provide the compound of formula V. Optional substituents can be introduced into the compound of formula V, as appropriate, according to methods known to those skilled in the art, to provide the desired compound of formula I.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The active compounds of this invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. In particular, the compounds of this invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The active compounds may also be useful in the treatment of additional disorders in which aberrant expression ligand/ receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, compounds of formula I may have therapeutic utility in inflammatory, angiogenic and immunologic disorders involving both identified and as yet unidentified tyrosine kinases that are inhibited by compounds of the formula I.

The in vitro activity of the active compounds in inhibiting the receptor tyrosine kinase (and thus subsequent proliferative response, e.g., cancer) may be determined by the following procedure.

Activity of the active compounds, in vitro, can be determined by the amount of inhibition of the phosphorylation of an exogenous substrate (e.g., Lys$_3$-Gastrin or polyGluTyr (4:1) random copolymer (I. Posner et al., *J. Biol. Chem.* 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, *Methods in Enzymology* 146, 82–88 (1987) from A431 cells (American Type Culture Collection, Rockville, Md.) and preincubated in a microfuge tube with EGF (2 $\mu$g/ml) in phosphorylation buffer +vanadate (PBV: 50 mM HEPES, pH 7.4; 125 mM NaCl; 24 mM MgCl$_2$; 100 $\mu$M sodium orthovanadate), in a total volume of 10 $\mu$l, for 20–30 minutes at room temperature. The test compound, dissolved in dimethylsulfoxide (DMSO), is diluted in PBV, and 10 $\mu$l, is mixed with the EGF receptor IEGF mix, and incubated for 10–30 minutes at 30° C. The phosphorylation reaction is initiated by addition of 20 $\mu$l $^{33}$P-ATP/substrate mix (120 $\mu$M Lys$_3$-Gastrin (sequence in single letter code for amino acids, KKKGPWLEEEEEAYGWLDF), 50 mM Hepes pH 7.4, 40 $\mu$M ATP, 2 $\mu$Ci γ-[$^{33}$P]-ATP) to the EGFr/EGF mix and incubated for 20 minutes at room temperature. The reaction is stopped by addition of 10 $\mu$l stop solution (0.5 M EDTA, pH 8; 2 mM ATP) and 6 $\mu$l 2N HCl. The tubes are centrifuged at 14,000 RPM, 4° C., for 10 minutes. 35 $\mu$l of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., lys$_3$-gastrin) is subtracted from all values as a background and percent inhibition is calculated relative to controls without test compound present.

Such assays, carried out with a range of doses of test compounds, allow the determination of an approximate IC$_{50}$ value for the in vitro inhibition of EGFR kinase activity. The compounds of the formula I that were tested using the procedure described above exhibited IC$_{50}$ values in the range of 0.0001–30 $\mu$M.

Activity of the active compounds, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep.* (Part 2)", 5, 169–186 (1975), with slight modifications. Tumors are induced in the left flank by s.c. injection of 1×10$^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic® P105 in 0.9% saline) by the intraperitoneal (ip) or oral (po) routes of administration twice daily i.e., every 12 hours) for 5 consecutive days. In order to determine an anti-tumor effect, the tumor is measured in millimeters with Vernier calipers across two diameters and the tumor size (mg) is calculated using the formula: Tumor weight=(length× [width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)=(TuW$_{control}$–TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates. The title compounds of the experimental examples of this case that are compounds of the formula I all exhibited, when tested in the above assay, percent inhibition values greater than 50% at 10 $\mu$M.

Other methods of assessing the activity of the compounds of the present invention are referred to in PCT international application publication number WO 95/21613 (published Aug. 17, 1995) which incorporated herein by reference.

Administration of the active compounds can be effected by any method that enables delivery of the compounds to the site of action (e.g., cancer cells). These methods include oral routes, intraduodenal routes, parenteral injection (including intravenous, subcutaneous, intramuscular, intravascular or infusion), topical administration, etc.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35mg/kg/day, in single or divided doses. For a 70 kg human, this would amount to about 0.05 to about 7 g/day, preferably about 0.2,to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for, example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5[N-(3,4-dihydro-2-methyl-4-oxoquinazolin6-ylmethyl)-N-methylamino]2-thenoyl)-L-glutamic acid; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4-cyano-3-(4-fluomphenylsulphonyl)-2hydroxy-2methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions, or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The following examples illustrate the preparation of the compounds of the invention. In the following examples, "Me" means methyl and "Et" means ethyl.

EXAMPLE 1
4-(6-Chloro2,3dihydro-indol-1-yl)-7H-pyrrolo[2,3-d]pyrimidine

To 4-chloro-7H-pyrrolo[2,3-d]pyrimidine (10.0 g, 0.065 mol) in dry pyridine (90 ml) was added 6chloro2,3dihydroindol-1-yl amine (14.8 g, 0.078 mol), and the mixture was heated in an 85° C. oil bath for 2 days. The reaction was cooled to ambient temperature and concentrated in vacuo. The resulting residue was purified by flash chromatography on silica gel (375 g, 40 mm mesh) using 5% MeOH/CH$_2$Cl$_2$ to afford the title compound as a pink-orange solid (1.1 g, 4.3%): HRMS: Calculated 271.0750, Found 271.0729; anal. RP18-HPLC RT: 4.88 minutes.

The above compound was dissolved in minimal methanol and a solution of HCl in (HCl(g) bubbled into 2 ml Et$_2$O)

was added dropwise until the mixture remained cloudy. The precipitated HCl salt was dried in vacuo, washed once with Et$_2$O, and dried in vacuo to constant mass (MP: 266° C. (dec)).

EXAMPLES 2–3

The compounds of Examples 2 and 3 were made according to the method of Example 1 from 4-chloro-7H-pyrrolo[2,3-d]pyrimidine and the appropriate amine starting material.

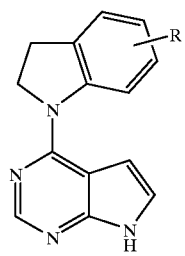

| Example no. | R | % Yield | RP18-HPLC RT | LC/MS (M$^+$) |
|---|---|---|---|---|
| 2 | 6-Methyl | 23 | 4.62 | 251 |
| 3 | 6-Chloro-5-fluoro | 23 | 4.66 | 289 |

EXAMPLE 4
1-(4-m-Tolylamino-pyrrolo[2,3-d]pyrimidin-7: yl)-ethanone

Following the procedure described in Example 1, (7H-Pyrrolo[2,3-d]pyrimidin4-yl)-m-tolyl-amine was prepared from 4-chloro-7H-pyrrolo[2,3-d]pyrimidine and m-toluidine (34%): HRMS: Calculated 225.1140, Found 225.1131; anal. RP18-HPLC RT: 3.45 min; HCl salt MP: 219° C.

To (3methyl-phenyl)-(7H-pyrrolo[2,3-d]pyrimidin4-yl)-amine (0.168 g, 0.75 mmol) dissolved in hot acetonitrile (7 ml) was added sodium hydride (36 mg, 0.90 mmol, 60% dispersion in mineral oil). After stirring at ambient temperature for 0.75 hour, acetyl chloride (0.11 ml, 1.5 mmol) was added and stirring continued for 48 hours. The mixture was concentrated in vacuo, triturated in hot ethyl acetate, and filtered. The filtrate was concentrated in vacuo to give an orange solid residue. The solid was triturated in CH$_2$Cl$_2$ and filtered to afford the title compound as a light yellow solid (0.11 g, 55%): LC-MS: 267 (MH$^+$); anal. RP18-HPLC RT: 3.53 minutes.

EXAMPLE 5
4-(6-Chloro-2,3dihydro-indol-1-yl)-pyrido[3,4-d]pyrimidine

To a suspension of 4-hydroxy-pyrido[3,4-d]pyrimidine (0.103 g, 0.70 mmol) in dry pyridine (2 ml) cooled in an ice-water bath was added dropwise trifluoroacetic anhydride (0.20 ml, 1.4 mmol). After stirring for 0.5 hour, 6-chloroindoline (0.10 g, 0.66 mmol) and pyridine (0.14 g, 1.81 mmol) in dry DMF (1.5 ml) was added dropwise. The cold bath was allowed to warm to ambient temperature and then heated at 70° C. for 3 hours. The reaction was cooled to ambient temperature and then added to methylene chloride (150 mL). The organic layer was washed with saturated sodium carbonate and water, and then dried over sodium sulfate. The solvent was removed by rotary evaporation and the residue purified by column chromatography (silica gel, 9/2/1-CH$_2$Cl$_2$/hexanes/methanol) to give a pale yellow residue (0.048 g, 28%): MP: 194–6° C.; LC/MS: 283 (MH$^+$).

EXAMPLES 6–8

The compounds of examples 6–8 were made according to the method of Example 5 from 4-chloro-pyrido[3,4-d]pyrimidine and appropriate amine starting materials.

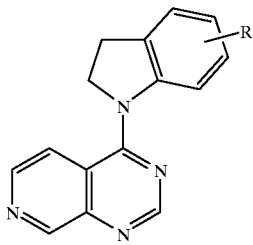

| Example # | R | Yield | HPLC RT | LC/MS (M$^+$) |
| --- | --- | --- | --- | --- |
| 6 | 6-Bromo-5-fluoro | 45 | 3.64 | 359 |
| 7 | 6-Chloro-5-fluoro | | | 315 |
| 8 | 6-Iodo | | | 389 |

EXAMPLE 9
(7-Benzenesulfonyl-7H-pyrrolo[2,3-d]pyrimidin-4-yl)-(3-ethynyl-phenyl)-amine To 4-chloro-7H-pyrrolo[2,3-d]pyrimidine (1.0 g, 0.0065 mol) in dry THF (10 ml) under nitrogen at −78° C. was added dropwise via syringe over 15 minutes n-butyllithium (2.5 M in hexane; 2.88 ml, 0.0072 mol). The cooling bath was removed and the solution was stirred for 1 hour. The resulting pyrrolo anion precipitated as a very fine white solid in a cloudy colorless solution. After the suspension was re-cooled to −78° C., benzenesulfonyl chloride (1.26 g, 0.0072 mol) was added neat via syringe. The resulting yellow mixture was allowed to warm slowly to ambient temperature overnight. The grey-white suspension was poured into 2% aqueous sodium bicarbonate (50 mL) and extracted with diethyl ether (4×20 mL). The combined extracts were washed with water and dried (potassium carbonate) and evaporated to give a light amber oil which crystallized from diethyl ether. The product was collected by filtration to 1.4 g (74%) of white solid: LC-MS=294 (MH$^+$); anal. RP18-HPLC RT: 4.40 minutes The above compound was dissolved in MeOH and m-aminophenyl acetylene (0.159 g, 0.0013 mol), and the mixture was heated in an 85° C. oil bath for 2 days. The reaction was cooled to ambient temperature and concentrated in vacuo. The residue was triturated with diethyl ether to produce a white solid (0.234 g. 92%): LC-MS: 375 (MH$^+$); anal. RP18-HPLC RT: 3.48 minutes.

EXAMPLE 10
4-(6Chloro-2,3dihydro-indol-1-yl)-5H-pyrrolo[3,2-d]pyrimidin-6-ol To a solution of 4(6Chloro-2,3-dihydro-indol-1-yl)-5-amino-6-methylacetyl-pyrimidine (541 mg, 1.55 mmol) in 40 mL of ethanol was added 25 mol % of 10% palladium on carbon (125 mg) and 0.11 mL of 1N HCl (1.55 mmol). The mixture was hydrogenated for 3 hours at 3.4 atm (50 psi)(H$_2$). The reaction is filtered through Celite® and concentrated in vacuo. The brown residue was slurried in methanol and the white solid was filtered off (279 mg, 63%): LC-MS: 287 (M$^+$); anal. RP18-HPLC RT: 5.61 minutes; MP: 250° C. (dec).

EXAMPLE 11
(3-Ethynyl-phenyl)-[7-(2-morpholin-4-yl-ethyl)-7H-pyrrolo[2,3-d]pyrimidin4-yl]-amine To a solution of 184 mg (1.4 mmol) of 4-(2-hydroxyethyl)morpholine in 10 mL of toluene was added 276 mg (2.0 mmol) of anhydrous potassium carbonate and then 32 mg (1.3 mmol) of 97% sodium hydride. After 30 minutes, 343 mg (1.0 mmol) of sulfonylated 4-chloro-7H-pyrrolo[2,3-d]pyrimidine was added and the reaction was heated at 100° C. for 2 hours. The reaction was then partitioned between ethyl acetate and water and the aqueous layer was extracted with two additional portions of ethyl acetate. The combined organic phase was washed with water, dried over magnesium sulfate and concentrated in vacuo. The residue was chromatographed on silica gel using 10% methanol/methylene chloride to give an amber oil (140 mg, 55%): LC-MS 267 (M$^+$).

The above compound was dissolved in MeOH and m-aminophenyl acetylene (0.123 g, 0.001 mol), and the mixture was heated in a sealed tube in a 120° C. oil bath for 12 hours. The reaction was cooled to ambient temperature and concentrated in vacuo. The residue was triturated with diethyl ether to produce a white solid (0.135 g, 74%): LC-MS=348 (MH$^+$); anal. RP18-HPLC RT: 3.33 minutes.

EXAMPLE 12
(3-Ethynyl-phenyl)-[7-(2-methoxy-ethyl)-7H-pyrrolo[2,3-d]pyrimidin-4-yl]-amine Following a procedure analogous to that described in Example 11, the title product was prepared in 81% yield from 4-chloro7-(2-methoxy-ethyl)-7H-pyrrolo[2,3-d]pyrimidine (1.0 eq) and m-aminophenyl acetylene (1.2 eq) in methanol: MP: 240–241° C.; LC-MS: 292 (MH$^+$); anal. RP18-HPLC RT: 4.16 minutes.

EXAMPLE 13
(3-Ethynyl-phenyl)-{7-[2-(2-methoxy-ethoxy)-ethyl]-7H-pyrrolo[2,3-d]pyrimidin4-yl}amine Following a procedure analogous to that described in Example 11, the title product was prepared in 81% yield from 4-chloro-7-[2-(2-methoxy-ethoxy)-ethyl]-7H-pyrrolo[2,3-d]pyrimidine (1.0 eq) and m-aminophenyl acetylene (1.2 eq) in methanol: MP: 240–241° C.; LC-MS: 336 (M$^+$); anal. RPP18-HPLC RT: 4.29 minutes.

EXAMPLE 14
(7-Allyl-pyrrolo[2,3-d]pyrimidin-4-yl)-(3-ethynyl-phenyl)-amine

To 4-chloro-7H-pyrrolo[2,3-d]pyrimidine (1.3 g: 8.5 mmol) in dry THF (30 ml) was added sodium hydride (1.0 g, 0.25 mmol, 60% dispersion in mineral oil). After stirring at ambient temperature for 1 hour, allyl iodide (0.93 ml, 10 mmol) was added and stirring continued for 48 hours. The mixture was concentrated in vacuo, triturated in hot ethyl acetate, and filtered. The filtrate was concentrated in vacuo to give an orange solid residue. The solid was triturated in CH$_2$Cl$_2$ and filtered to afford 4-chloro-7-allyl-pyrrolo[2,3-d]pyrimidine as a light yellow powder (0.58 g, 36%): TS-MS: 194 (MH$^+$).

To 4-chloro-7-allyl-pyrrolo[2,3-d]pyrimidine (0.5 g, 2.6 mmol) in dry MeOH (5 ml) was added m-aminophenyl acetylene (0.36 g, 3.1 mmol). The suspension was heated in a sealed pressure tube at 125° C. for 20 hours. The reaction was cooled to ambient temperature and concentrated in vacuo. The resulting oil was purified by flash chromatography on silica gel (50 g, 40 mm mesh) using 3% MeOH/CH$_2$Cl$_2$ to afford the title compound as a yellow powder (0.29 g, 41%): TS-MS: 275 (MH$^+$); anal. RP18-HPLC RT: 4.62 minutes.

EXAMPLE 15

N-(5-Iodo-7H-pyrrolo[2,3-d]pyrimidin4-yl)-N-m-tolyl-acetamide

To (3-methyl-phenyl)-(7H-pyrrolo[2,3-d]pyrimidin4-yl)-amine (0.75 g, 3.4 mmol) dissolved in hot acetonitrile (30 ml) was added sodium hydride (0.16 g, 4.0 mmol, 60% dispersion in mineral oil). After stirring at ambient temperature for 0.75 hour, acetyl chloride (0.48 ml, 6.7 mmol) was added and the mixture was stirred for 48 hours. The mixture was concentrated in vacuo, triturated in hot ethyl acetate, and filtered. The filtrate was concentrated in vacuo to give an orange solid residue. The solid was purified by flash chromatography on silica gel (13 g, 40 mm mesh) using 1:3 ethyl acetate/hexanes to afford the title product as a yellow solid (0.21 g): TS-MS: 309 (MH$^+$).

To 1-(4-m-tolylamino-pyrrolo[2,3-d]pyrimidin-7-yl)-ethanone (0.21 g, 0.79 mmol) in dry $CH_2Cl_2$ (5 ml) and dry MeOH (2 ml) was added $Na_2CO_3$ (0.17 g, 1.6 mmol). After stirring at ambient temperature for 0.75 hour, N-iodosuccinimide (0.35 g, 1.6 mmol) was added. The mixture was stirred at ambient temperature for 48 hours then concentrated in vacuo. The residue was diluted with $CH_2Cl_2$ and $H_2O$. The $H_2O$ phase was extracted once with $CH_2Cl_2$. The organic phase was washed twice with $H_2O$, dried over $Na_2SO_4$, and concentrated in vacuo. The resulting residue was purified by flash chromatography on silica gel (11 g, 40 mm mesh) using 2% MeOH/$CH_2Cl_2$ to afford the title compound as a yellow solid (30 mg): TS-MS: 393 (MH$^+$); anal. RP18-HPLC RT: 3.42 minutes.

EXAMPLE 16

4-(6Chloro-2,3-dihydro-indol-1-yl)-6methyl-pyrido[3,4-d]pyrimidine

6Methyl-pyrido[3,4-d]pyrimid-4one (200 mg, 1.24 mmol), polymer-supported triphenylphosphine (2.06 g of 3.0 mmol Pig resin, 6.20 mmol) and anhydrous carbon tetrachloride (1.20 mL, 12.40 mmol) were combined in 1,2-dichloroethane (6 mL). The mixture was heated to 60° C. under an atmosphere of dry $N_2(g)$ for 18 hours. 6-Chloroindoline (1.1 eq.) was added and heating was continued at 60° C. for another 18 hours. The triphenyphosphine-bearing resin was filtered off and washed several times with chloroform. The filtrate and washings were concentrated in vacuo and preparative reversed-phase (C18) chromatography utilizing a gradient of 15% to 70% MeCN/pH4.5, 50 mM $NH_4OAc$ followed by lyophilization of the appropriate fractions afforded the title product (30%) as its free-base: MP: 232–234° C.; LC-MS: 297 (MH$^+$); anal. RP-HPLC: 4.33 minutes.

EXAMPLES 17–19

The compounds of examples 17–19 were made according to the method of Example 16 from 4-chloro6-methyl-pyrido[3,4-d]pyrimidine and the appropriate amine starting materials.

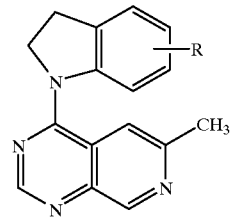

| Example no. | R | Yield | RP18-HPLC RT | LC/MS (M$^+$) |
|---|---|---|---|---|
| 17 | 6-Bromo-5-fluoro | 45 | 3.64 | 359 |
| 18 | 6-Chloro-5-fluoro | | | 315 |
| 19 | 6-Iodo | | | 389 |

EXAMPLE 20

4-(4-Bromo-7-methyl-2,3-dihydro-indol-1-yl)-6-methyl-pyrido[3,4-d]pyrimidine hydrochloride salt The title product was prepared from 6methyl-pyrido[3,4-d]pyrimid-4-one (1.0 eq.) and 4-bromo-7-methyl-indoline (1.5 eq.) according to the procedure described for Example 16. The crude product from the filtrate was flash chromatographed on silica using EtOAc/hexanes/MeOH (9:2:1) to afford the free base which was converted to the hydrochloride salt as described for Example 23 (33% yield): MP: 232–244° C.; LC-MS: 355, 357 (MH$^+$); anal. RP-HPLC: 5.20 minutes.

EXAMPLE 21

4-(6-Bromo-7-methyl-2,3-dihydro-indol-1-yl)-6-methyl-pyrido[3,4-d]pyrimidine hydrochloride salt The title product was prepared from 6-methyl-pyrido[3,4-d]pyrimid-4-one (1.0 eq.) and 6-bromo-7-methyl-indoline (1.5 eq.) according to the procedure described for Example 16. The crude product from the filtrate was flash chromatographed on silica using EtOAc/hexanes/MeOH (9:2:1) to afford the free base which was converted to the hydrochloride salt as described for Example 23 (34% yield): MP 212–229° C.; LC-MS: 355, 357 (MH$^+$); anal. RP-HPLC: 4.90 minutes.

EXAMPLE 22

4-(6-Bromo-5-fluoro-2,3dihydro-i ndol-1-yl)-6-methyl-pyrido[3,4-d]pyrimidine hydrochloride salt The title product was prepared from 6-methyl-pyrido[3,4-d]pyrimid-4-one (1.0 eq.) and 6-bromo-5-fluoro-indoline (1.5 eq.) according to the procedure described for Example 16. The crude product from the filtrate was flash chromatographed on silica using 2% MeOH/98% $CH_2Cl_2$ to afford the free base which was converted to the hydrochloride salt as described for Example 23 (36% yield): MP: 262–264° C.; LC-MS: 359, 361 (MH$^+$); anal. RP-HPLC: 4.83 minutes.

EXAMPLE 23

4-(6,7-Dimethyl-2,3-dihydro-indol-1-yl)pyrido[3,4-d]pyrimidine

To 4-chloro-pyrido[3,4-d]pyrimidine (200 mg, 1.21 mmol) in isopropanol (3 mL) was added 6,7-dimethylindoline (211 mg, 1.44 mmol) and pyridine (190 mg, 2.41 mmol). The mixture was heated to reflux under an atmosphere of dry $N_2(g)$ for 6hours. Solvent was removed in vacuo and the residue was dissolved in $CHCl_3$ and washed with saturated aqueous $Na_2CO_3$. The organic phase was dried over $Na_2SO_4$, concentrated in vacuo, and flash chromatographed on silica in 45% acetone/hexanes to afford 60 mg of 4-(6,7dimethyl-2,3-dihydro-indol-1-yl)-pyrido[3,4-d]pyrimidine (LC-MS: 278 (MH$^+$). This material was dissolved in a minimum volume of 10% MeOH in CH$_2$Cl$_2$, and 1 mole equivalent of HCl in diethyl ether was added dropwise with stirring. The mixture was diluted with diethyl ether (4 volumes) and the precipitated HCl salt of the product was filtered and dried in vacuo (58 mg): MP: 248° C.; GEMS: 277 (M$^+$); anal. RP-HPLC: 4.06 minutes.

EXAMPLE 24
(3-Ethynyl-phenyl)-pyrido[3,4-d]pyrimidin-4-yl-amine

To 4-chloro-pyrido[3,4-d]pyrimidine (250 mg, 1.50 mmol) in N-methylpyrrolidin-2-one (0.5 mL) was added 3ethynylaniline (212 mg, 1.81 mmol) and pyridine (237 mg, 3.0 mmol). The mixture was heated to 80° C. under an atmosphere of dry N$_2$(g) for 3 hours. The reaction mixture was dissolved in CHCl$_3$ and washed with saturated aqueous Na$_2$CO$_3$, and brine. The organic phase was dried over Na$_2$SO$_4$, concentrated in vacuo, and flash chromatographed on silica with a gradient of 40% to 70% acetone/hexanes to afford 120 mg of product. This material was precipitated as its hydrochloride salt by dissolution in minimal CHCl$_3$, titration with HCl (1 eq.) in diethyl ether, and dilution with diethyl ether. The yellow salt was filtered and dried in vacuo (133 mg): MP 233–235° C.; LC-MS: 247 (MH$^+$); anal. RP-HPLC: 3.45 minutes.

EXAMPLE 25
Benzo[b]thiophen-5-yl-pyrido[3,4-d]pyrimidin-4-yl-amine

To 4-chloro-pyrido[3,4-d]pyrimidine (250 mg, 1.50 mmol) in N-methylpyrrolidin-2-one (0.5 mL) was added benzo[b]thiophen-5-yl-amine (270 mg, 1.81 mmol) and pyridine (237 mg, 3.0 mmol). The mixture was heated to 80° C. under an atmosphere of dry N$_2$(g) for 3 hours. The reaction mixture was dissolved in CHCl$_3$ and washed with saturated aqueous Na$_2$CO$_3$, and brine. The organic phase was dried over Na$_2$SO$_4$(s), concentrated in vacuo, and flash chromatographed on silica in 40% to 70% acetone/hexanes to afford 180 mg of product. This material was precipitated as its hydrochloride salt by dissolution in minimal CHCl$_3$, tritration with HCl (1 eq.) in diethyl ether, and dilution with diethyl ether. The yellow salt was filtered and dried in vacuo (188 mg): MP: 280–282° C.; LC-MS: 279 (MH$^+$); anal. RP-HPLC: 3.63 minutes.

EXAMPLE 26
(3-Ethynyl-phenyl)-(5-p-tolyl-7H-pyrrolo[2,3-d]pyrimidin4-yl)-amine To a solution of 7-Benzenesulfonyl-4-chloro-5-iodo-7H-pyrrolo[2,3-d]pyrimidine (400 mg, 0.953 mmol) in 8 mL of toluene was added this (benzylidene acetone) dipalladium chloroform adduct (40 mg, 10% by weight), 4-methyl benzene boronic acid (260 mg, 1.91 mmol), sodium carbonate solution (2.86 ml of 1 M solution) and 3.0 ml of ethanol (absolute). The mixture was refluxed for seven hours. The reaction mixture was filtered through Celite®, and the Celite® was washed with ethyl acetate. The filtrate was poured into a separatory funnel was washed with saturated sodium bicarbonate (100 mL, 2 times). The organic layer was dried over magnesium sulfate and concentrated in vacuo. The resulting green black oil was stirred in methanol (5 mL) and KOH (107 mg, 1.91 mmol in 3 mL of water) was added. After three hours, the reaction mixture was concentrated and the residue dissolved in water. The solution was acidified with 1 N HCl and extracted with ethyl acetate (50 ml, 3 times). The organic layer was dried over MgSO$_4$ and concentrated in vacuo. The resulting oil was chromatographed on silica gel (180 g, 40 μm) using 30% ethyl acetate/hexanes to provide the product as a white solid (225 mg 92%): TS-MS: 244, 246 (MH$^+$). To 4-chloro-(5-p-tolyl)-7H-pyrrolo[2,3-d] pyrimidine (200 mg, 0.821 mmol) in dry methanol (4 mL) was added m-aminophynel acetylene (106 mg, 0.903 mmol). The suspension was heated in a sealed tube at 120° C. for 18 hours. The reaction was cooled to ambient temperature and concentrated in vacuo to a brown solid. The residue was chromatographed over silica gel (140 g, 40 μm) using 40% ethyl acetate/hexanes to provide the title compound as a light yellow solid (82 mg, 32%): MP: 245–247° C.; anal. RP18-HPLC RT: 6.120 minutes.

EXAMPLE 27
(3-Ethynyl-phenyl)-(5-thiophen-2-yl-7H-pyrrolo[2,3-d]pyrimidin4-yl]-amine Following the procedure described in Example 26, the title compound was prepared in 40% yield from 7-Benzenesulfonyl-4-chloro-5-iodo-7H-pyrrolo[2,3-d]pyrimidine and thiophene-2-boronic acid followed by coupling with m-aminophenyl acetylene (27 mg, 0.233 mmoles) in methanol: MP: 230–232° C.; TS-MS: 317 (MH$^+$); anal. RP18-HPLC RT: 5.614 minutes.

EXAMPLE 28
(3-Ethynyl-phenyl-[5-(4-methoxy-phenyl)-7H-pyrrolo[2,3-d]pyrimidin-4-yl]-amine Following the procedure described in Example 26, 4-chloro-[5-(4-methoxy-phenyl)]-7H-pyrrolo[2,3-d]pyrimidine, the intermediate, was made in 74% yield from 7-benzenesulfonyl-4-chloro-5-iodo-7H-pyrrolo[2,3-d]pyrimidine and 4-methoxy benzene boronic acid: TS-MS: 260 (MH$^+$). The title compound was synthesized by coupling the intermediate with m-aminophenyl acetylene in 75%yield: MP: 207–210° C.; FAB MS: 341 (MH$^+$); anal. RP18-HPLC RT=5.640 minutes.

EXAMPLE 29
(3-Ethynyl-phenyl)-[5-3-nitro-phenyl)-7H-pyrrolo[2,3-d]pyrimidin-4-yl]-amine Following the procedure described in Example 26, 4-chloro-[5(4-methoxy-phenyl)]-7H-pyrrolo[2,3-d]pyrimidine, the intermediate, was made in 74% yield from 7-benzenesulfonyl-4-chloro-5iodo-7H-pyrrolo[2,3-d]pyrimidine and 3nitro benzene boronic acid: TS-MS: 260 (MH$^+$). The title compound was synthesized from coupling the intermediate with m-aminophenyl acetylene in 15% yield: MP 189–190° C.; TSMS: 469 (MH$^+$); anal. RP18-HPLC RT=4.67 minutes.

EXAMPLE 30
[5-(4-chloro-phenyl)-7H-pyrrolo[2,3-d]pyrimidin-4-yl]-(3-ethynyl-phenyl)-amine Following the procedure described in Example 26, 4-chloro-[5-(4-methoxy-phenyl)]-7H-pyrrolo[2,3-d]pyrimidine, the intermediate, was made in 74% yield from 7-benzenesulfonyl-4-chloro-5iodo-7H-pyrrolo[2,3-d]pyrimidine and 4-chloro benzene boronic acid: TS-MS: 260 (MH$^+$). The title compound was synthesized by coupling the intermediate with m-aminophenyl acetylene in 33% yield: MP: 225–227° C.; TSMS: 398 (MH$^+$); anal. RP18-HPLC RT=6.45 minutes.

EXAMPLE 31
(3-Bromo-phenyl)-(6bromo-5-phenyl-7H-pyrrolo[2,3-d]pyrimidin-4-yl)-amine Utilizing an analogous procedure as described in Example 26, 4-chloro-(5-phenyl)-7H-pyrrolo[2,3-d] pyrimidine, the intermediate, was made in 74% yield from 7-benzenesulfonyl-4-chloro-5iodo-7H-pyrrolo[2,3-d]pyrimidine and 3-bromo benzene boronic acid: TS-MS: 230 (MH⁺) This second intermediate was coupled with 3-bromoaniline in methanol in a sealed tube to provide (3-bromo-phenyl)-[5-(4-chloro-phenyl)7H-pyrrolo[2,3-d]pyrimidin-4-yl]-amine in 75% yield: TSMS: 365 (MH+). (3-bromo-phenyl)-[5-(4-chloro-phenyl)-7H-pyrrolo[2,3-d]pyrimidin-4-yl]-amine was brominated with N-bromosuccinimide impregnated onto silica gel. The reaction was complete after stirring at room temperature under nitrogen for 1.5 hours. The reaction was filtered and concentrated in vacuo to provide the title compound as a gray solid in 28% yield (128 mg): MP.: dec 300° C.; TSMS: 445/447 (MH⁺/MH⁺2); anal. RP1 8-HPLC RT=7.223 minutes.

What is claimed is:

1. A compound of the formula

I or a pharmaceutically acceptable salt thereof, wherein:

Z is a group of the formula

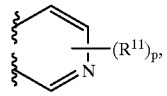

(Ia)

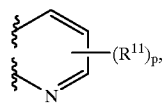

(Ib)

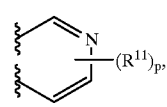

(Ic)

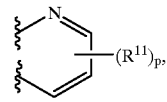

(Id)

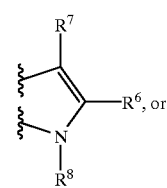

(Ie)

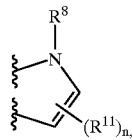

(If)

wherein n is an integer from 0 to 2 and p is an integer from 0 to 3;

$R^1$ is H, $C_1$–$C_6$ alkyl or —C(O)($C_1$ $C_6$ alkyl);

$R^2$ is 1H-indazol-5-yl, wherein said groups are optionally substituted by 1 to 3 $R^5$ substituents, or $R^2$ is a group of the formula (Ii) or (Ij)

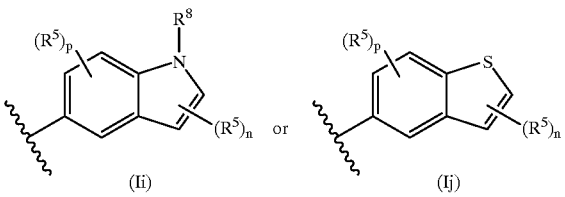

(Ii)                    (Ij)

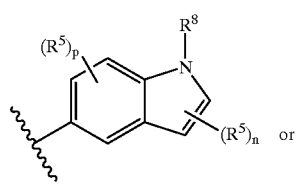

(Ii)

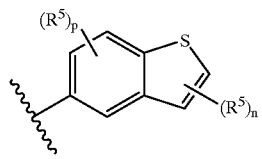

(Ij)

wherein p is an integer from 0 to 3 and n is an integer from 0 to 2;

or $R^1$ and $R^2$ are taken together to form a group of the formula (Ik)

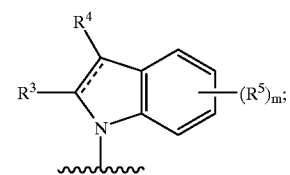

(Ik)

wherein the dashed line indicates a single or double bond and m is an integer from 0 to 4;

each $R^3$ is independently H, —C(O)O$R^9$, or $C_1$–$C_6$ alkyl wherein said alkyl is optionally substituted by halo, —O$R^9$, —N$R^9R^{10}$, or —C(O)O$R^9$;

$R^4$ is $R^3$, —O$R^9$, or —N$R^9R^{10}$;

each $R^5$ is independently halo, cyano, $C_1$–$C_6$ alkyl, $C_2$–$C_6$ alkenyl, $C_2$–$C_5$ alkynyl, —O$R^9$, —N$R^9R^{10}$, nitro, or $C_6$–$C_{10}$ aryl wherein said alkyl, alkenyl, alkynyl and aryl $R^5$ groups are optionally substituted by 1 to 3 substituents independently selected from halo, nitro, $C_1$–$C_4$ alkyl and —O$R^9$;

$R^6$ and $R^7$ are independently H or $R^5$;

$R^8$ is H, —SO$_2$(C$_6$–C$_{10}$aryl), (CH$_2$)$_q$(5–10 membered heterocyclyl), C$_2$–C$_6$ alkenyl, C$_1$–C$_6$ alkyl, —(CH$_2$)$_q$O (CH$_2$)$_q$(C$_1$–C$_6$ alkoxy), —(CH$_2$)$_q$(C$_{1-C6}$ alkoxy), —C(O)(C$_1$–C$_6$ alkoxy), or —SO$_2$(C$_1$–C$_4$ alkyl) wherein each q is independently an integer from 2 to 4;

each $R^9$ and $R^{10}$ is independently H or C$_1$–C$_6$ alkyl; and, $R^{11}$ is trifluoromethyl, halo, nitro, —OR$^9$, —NR$^9$R$^{10}$, cyano, C$_1$–C$_4$ alkyl, —S(O)$_x$R$^9$ wherein x is an integer from 0 to 2,—C(O)OR$^9$, —OC(O)(C$_1$–C$_4$ alkyl), —C(O)NR$^9$R$^{10}$, —NR$^9$C(O)(C$_1$–C$_4$ alkyl), —C(O)NHSO$_2$(C$_1$–C$_4$ alkyl), —NHCH$_2$C(O)NR$^9$R$^{10}$, —NHC(O)(C$_1$–C$_4$ alkoxy), —NHOC(O)(C$_1$–C$_4$ alkyl), —NR$^9$OR$^{10}$, anilino, pyrrolidinyl, piperidinyl, azido, guanidino, phenyl, —C(O)(C$_1$–C$_6$ alkyl), benzenesulfonyl, allyl, thiophenyl, morpholino, piperazinyl, 4-(C$_1$–C$_4$ alkyl)piperazinyl, phenylthio, benzenesulphonamido, 2-oxopyrrolidin-1-yl, 2,S-dioxopyrrolidin-1-yl, phenoxy, benzoyloxy, benzoylamino, —CH$_2$)$_w$O(CH$_2$)$_v$OR$^9$, —O(CH$_2$)$_w$O (CH$_2$)$_v$OR$^9$, —O(CH$_2$)$_w$C(O)OR$^9$, —O(CH$_2$)$_w$ C(O) NR$^9$R$^{10}$, —(CH$_2$)$_w$S(CH$_2$)$_v$OR$^9$, —NH (CH$_2$)$_v$O (C$_1$–C$_4$ alkyl), —NH(CH$_2$)$_w$(C$_6$–C$_{10}$ aryl), —NHC(O) (CH$_2$)$_w$(C$_1$–C$_4$ alkoxy), or —O(CH$_2$)$_w$(C$_6$–C$_{10}$, aryl), wherein w is an integer from 1 to 4 and v is an integer from 2 to 4, and wherein the alkyl, heterocyclic, and aryl moieties of the foregoing $R^{11}$ groups are optionally substituted by 1 or 2 substituents independently selected from the group consisting of halo, C$_1$–C$_4$ alkyl, —OR$^9$, —NR$^9$R$^{10}$, —C(O)OR$^9$, —OC(O) (C$_1$–C$_4$ alkyl), —C(O)NR$^9$R$^{10}$, —NHC(O)(C$_1$–C$_4$ alkyl), nitro, imidazolyl, piperidino, morpholino, and piperazinyl.

2. A compound selected from the group consisting of:

4-(6-Chloro-2,3dihydro-indol-1-yl)-7H-pyrrolo[2,3-d] pyrimidine;

4-(6-Methyl-2,3-dihydro-indol-1-yl)-7H-pyrrolo[2,3-d] pyrimidine;

4-(6-Chloro-5-fluoro-2,3dihydro-indol-1-yl)-7H-pyrrolo [2,3-d]pyrimidine;

4-(6-Chloro-2,3dihydro-indol-1-yl)-pyrido[3,4-d] pyrimidine;

4-(6-Bromo-5-chloro-2,3-dihydro-indol-1-yl)-pyrido[3,4-d]pyrimidine;

4-(6-Fluoro-5-chloro-2,3dihydro-indol-1-yl)-pyrido[3,4-d]pyrimidine;

4-(6-Iodo-2,3-dihydro-indol-1-yl)pyrido[3,4-d] pyrimidine;

4-(6-Chloro-2,3dihydro-indol-1-yl)-5H-pyrrolo[3,2-d] pyrimidin-6-ol; 4-(6-Chloro-2,3'-dihydro-indol-1-yl)-6-methyl-pyrido[3,4-d]pyrimidine;

4-(6-Bromo-5-fluoro-2,3-dihydro-indol-1-yl)-6-methyl-pyrido[3,4-d]pyrimidine;

4-(6-Chloro-5-fluoro-2,3-dihydro-indol-1-yl)-6-methyl-pyrido[3,4-d]pyrimidine;

4-(6-Iodo-2,3dihydro-indol-1-yl)6-methyl-pyrido[3,4-d] pyrimidine;

4-(4-Bromo-7-methyl-2,3-dihydro-indol-1-yl)-6-methyl-pyrido [3,4-d]pyrimidine;

4-(6-Bromo-7-methyl-2,3-dihydro-indol-1-yl)-6-methyl-pyrido[3,4-d]pyrimidine;

4-(6,7-Dimethyl-2,3dihydro-indol-1-yl)pyrido[3,4-d] pyrimidine;

Benzo[b]thiophen-5-yl-pyrido[3,4-d]pyrimidin-4-yl-amine; and the pharmaceutically acceptable salts of the foregoing compounds.

3. A pharmaceutical composition for the treatment of a hyperproliferative disorder in a mammal which comprises a therapeutically effective amount of a compound of claim 1 and a pharmaceutically acceptable carrier.

4. The pharmaceutical composition of claim 3 wherein said hyperproliferative disorder is cancer.

5. The pharmaceutical composition of claim 4 wherein said cancer is brain, lung, kidney, renal, ovarian, squamous cell, bladder, gastric, pancreatic, breast, head, neck, oesophageal, gynecological, prostate, colorectal or thyroid cancer.

6. The pharmaceutical composition of claim 3 wherein said hyperproliferative disorder is noncancerous.

7. The pharmaceutical composition of claim 6 wherein said disorder is a benign hyperplasia of the skin or prostate.

8. A pharmaceutical composition for the treatment of a hyperproliferative disorder in a mammal which comprises a therapeutically effective amount of a compound of claim 1 in combination with an anti-tumor agent selected from the group consisting of mitotic inhibitors, alkylating agents, anti-metabolites, intercalating antibiotics, enzymes, topoisomerase inhibitors, biological response modifiers, anti-hormones, and anti-androgens, and a pharmaceutically acceptable carrier.

9. A pharmaceutical composition for the treatment of pancreatitis or kidney disease in a mammal which comprises a therapeutically effective amount of a compound of claim 1 and a pharmaceutically acceptable carrier.

10. A pharmaceutical composition for the blastocyte implantation in a mammal which comprises a therapeutically effective amount of a compound of claim 1 and a pharmaceutically acceptable carrier.

11. A pharmaceutical composition for treating a disease related to vasculogenesis or angiogenesis in a mammal which comprises a therapeutically effective amount of a compound of claim 1 and a pharmaceutically acceptable carrier.

12. The pharmaceutical composition of claim 11 wherein said disease is selected from the group consisting of diabetes, diabetic retinopathy, hemangioma, glioma, melanoma, Kaposi's sarcoma, ovarian cancer, breast cancer, lung cancer, pancreatic cancer, prostate cancer, colon cancer and epidermoid cancer.

13. A method of treating a hyperproliferative disorder in a mammal which comprises administering to said mammal a therapeutically effective amount of a compound of claim 1.

14. The method of claim 12 wherein said hyperproliferative disorder is cancer.

15. The method of claim 14 wherein said cancer is brain, lung, squamous cell, renal, kidney, ovarian, bladder, gastric, pancreatic, breast, head, neck, oesophageal, prostate, colorectal, gynecological or thyroid cancer.

16. The method of claim 13 wherein said hyperproliferative disorder is noncancerous.

17. The method of claim 16 wherein said disorder is a benign hyperplasia of the skin or prostate.

18. A method for the treatment of a hyperproliferative disorder in a mammal which comprises administering to said mammal a therapeutically effective amount of a compound of claim 1 in combination with an anti-tumor agent selected from the group consisting of mitotic inhibitors, alkylating agents, anti-metabolites, intercalating antibiotics, enzymes, topoisomerase inhibitors, biological response modifiers, anti-hormones, and anti-androgens.

19. A method of treating pancreatitis or kidney disease in a mammal which Comprises administering to said mammal a therapeutically effective amount of a compound of claim 1.

20. A method of preventing blastocyte implantation in a mammal which comprises administering to said mammal a therapeutically effective amount of a compound of claim 1.

21. A method for treating a disease related to vasculogenesis or angiogenesis in a mammal which comprises administering to said mammal a therapeutically effective amount of a compound of claim 1.

22. The method of claim 21 wherein said disease is selected from the group consisting of diabetes, diabetic retinopathy, hemangioma, glioma, melanoma, Kaposi's sarcoma, ovarian cancer, breast cancer, lung cancer, pancreatic cancer, prostate cancer, colon cancer and epidermoid cancer.

* * * * *